United States Patent [19]

Kusano et al.

[11] Patent Number: 4,634,381
[45] Date of Patent: Jan. 6, 1987

[54] PARTIAL DENTAL PROSTHESIS

[75] Inventors: Takae Kusano; Masato Ueno, both of Hiroshima, Japan

[73] Assignees: Molten Corp.; Kabushiki Kaisha Four Brain, both of Hiroshima, Japan

[21] Appl. No.: 728,129

[22] Filed: Apr. 29, 1985

[30] Foreign Application Priority Data

May 16, 1984 [JP] Japan .................................. 59-99309

[51] Int. Cl.[4] .............................................. A61C 13/22
[52] U.S. Cl. .................................. 433/172; 433/168.1
[58] Field of Search ............... 433/184, 185, 188, 168, 433/172

[56] References Cited

U.S. PATENT DOCUMENTS

| | | | |
|---|---|---|---|
| 2,897,594 | 8/1959 | Kopec et al. | 433/185 |
| 3,886,659 | 6/1975 | Reifke | 433/188 |
| 4,193,194 | 3/1980 | Dalise | 433/177 |
| 4,380,434 | 4/1983 | Weissman | 433/177 |

Primary Examiner—Robert Peshock
Attorney, Agent, or Firm—Armstrong, Nikaido, Marmelstein & Kubovcik

[57] ABSTRACT

In accordance with the present invention, there can be provided a partial dental prosthesis comprising artificial teeth and a denture base holding the artificial teeth, wherein at least one end of the partial dental prosthesis is adjacent to a retentive tooth, which is improved in that a projecting member made of an elastic material is provided at one or two ends of the partial dental prosthesis so as to be closely or elastically in contact with an undercut of the natural tooth. The partial dental prosthesis does not cause natural teeth adjacent to the partial dental prosthesis to be damaged and can be stably and steadily supported on an alveolus ridge of a patient.

7 Claims, 13 Drawing Figures

PARTIAL DENTAL PROSTHESIS

BACKGROUND OF THE INVENTION

The present invention relates to a partial dental prosthesis, and, more particularly, to a partial dental prosthesis which does not cause natural teeth adjacent to the partial dental prosthesis to be damaged and can be stably and steadily supported on an alveolus ridge of the patient.

In FIG. 11 and FIG. 12, which are a plan view showing a typical conventional partial dental prosthesis used widely and a sectional view taken along a line E—E in FIG. 11, respectively, the partial dental prosthesis 1 comprises artificial teeth 2; a denture base 3 holding the artificial teeth 2; wire type clasps 4 provided at both ends of the denture base 3; and a part of an attachment 6 being formed at a side portion of the artificial tooth 2 facing to a side portion of the natural tooth 9 at which the other part of the attachment 6 is formed. At the side portion of the artificial tooth 2, the attachment 6 has a metallic ball 5, a spring 7 urging the ball 5 from the side portion of the artificial tooth 2 toward the side portion of the natural tooth 9 of the patient and a metallic casing 8 in which the ball 5 and the spring 7 are contained. Further, at the side portion of the natural tooth 9, the attachment 6 has a circular concave 10 in which the surface of the ball 5 is partially received when the ball bearing 5 is urged by the spring 7. Numeral 11 indicates an alveolus ridge on which the partial dental prosthesis 1 is supported. The partial dental prosthesis is supported on the alveolus ridge 11 by urging the ball 5 to the circular concave 10 with the spring 7 and by anchoring to the natural teeth 9 with the wire type clasp 4.

In the above described partial dental prosthesis 1, there are several problems, as follows:

(1) The force applied to the natural tooth by the wire type clasp is not always uniform, since the wire type clasp is made of metal which tends to apply a large localized force to the natural tooth. Accordingly, the life span of the natural tooth to be clasped are shortened.

(2) Due to the repeated use of the partial dental prosthesis in the mouth, the wire type clasp is plastically deformed. Therefore, the fixing function of the wire type clasp is reduced. As a result, the partial dental prosthsis supported on the alveolus ridge becomes unstable and unsteady. In that case, it is necessary to correct the shape of the wire type clasp to the original shape;

(3) The wire type clasp is usually provided at a portion where one can see from outside. Accordingly, such an appearence is not preferable from an aesthetic point of view;

(4) The wire type clasp made of metal causes a patient to unpleasantly feel it as an extraneous substance;

(5) The attachment is weak in strength, and insufficient in durability, since the attachment 6 is assembled from very small elements;

(6) The cost of the attachment is high, since the attachment has to be manufactured by precise and fine technique;

(7) The attachment has a problem concerning sanitation, since saliva, dregs in the mouth, and the like are easily stayed in the metallic casing and it is much difficult to clean the interior of the metallic casing.

An object of the invention is to provide a partial dental prosthesis which does not cause natural teeth adjacent to the partial dental prosthesis to be damaged and can be stably and steadily supported on an alveolus ridge of the patient.

SUMMARY OF THE INVENTION

In accordance with the present invention, there can be provided a partial dental prosthesis comprising artificial teeth and a denture base holding the artificial teeth, wherein at least one end of the partial dental prothesis is adjacent to a retentive tooth, which is improved in that a projecting member made of an elastic material is provided at one or two ends of the partial dental prosthesis so as to be closely or elastically in contact with an undercut of the natural tooth, whereby the partial dental prosthesis can be stably and steadily supported on an alveolus ridge of a patient.

The above and other objects and the advantages of the present invention will become apparent from the following description with the accompanying drawings.

DETAILED DESCRIPTION OF THE INVENTION

Figure 1:
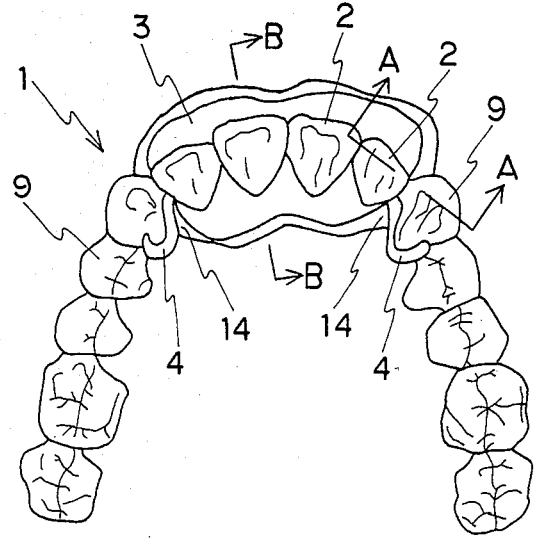
FIG. 1 is a plan view showing an embodiment of the partial dental prosthesis of the present invention.
Figure 2:
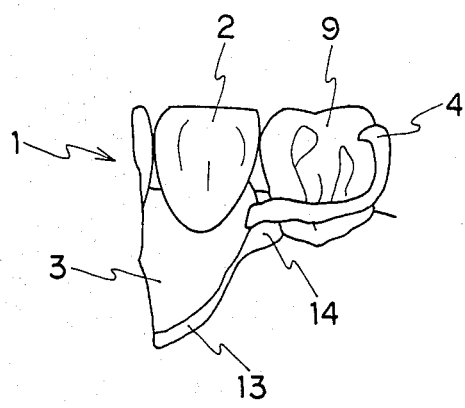
FIG. 2 is a partial side elevational view of the partial dental prosthesis shown in FIG. 1.
Figure 3:
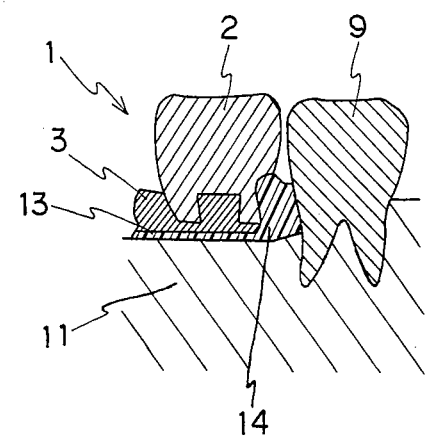
FIG. 3 is a sectional view taken along a line A—A in FIG. 1.
Figure 4:
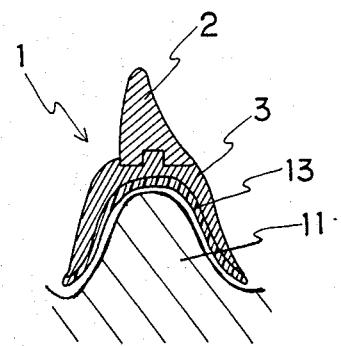
FIG. 4 is a sectional view taken along a line B—B in FIG. 1.

FIGS. 1 to 4 show an embodiment of the partial dental prosthesis of the present invention. In this embodiment, a partial dental prosthesis 1 has artificial teeth 2. The artificial teeth 2 are held on a denture base 3. Clasps 4, 4 reduced in size are provided at both ends of the denture base 3. The clasp 4 is defined at the portion of a retentive tooth where one cannot see from outside, i.e. at tongue side of the retentive tooth. An elastic lining layer 13 made of an elastic material is provided over an inner surface of the denture base 3. The denture base 3 is made of a hard polymer material. In the present invention, it is preferable to employ a thermosetting or crosslinkable polymer as a material of the denture base, and a thermoplastic elastomer as the elastic lining layer. Numerals 14, 14 indicate projecting members provided at both ends of the partial dental prosthesis 1. The projecting member 14 functions as a means for fixing the partial dental prosthesis 1 on the alveolus ridge 11. Preferably, the projecting member 14 and the elastic lining layer 13 are integrally formed, as described later. The projecting member 14 is adapted to be closely or elastically in contact with an undercut having a downward taper (shown in FIG. 3) of the retentive tooth 9 adjacent to the artificial tooth 2 so that a denture retention by means of the projecting member 14 can be caused to the undercut when the partial dental prosthesis 1 is set in a mouth of a patient. The projecting member 14 preferably has a shape approximately corresponds to the shape of the undercut of the retentive tooth adjacent to the artificial tooth 2.

When the partial dental prosthesis 1 is set in the mouth of the patient, the projecting member 14 is in contact with the undercut of the retentive tooth. The projecting member 14 causes uniform denture retention to the undercut of the retentive tooth. Further, since the projecting member 14 is closely and elastically in contact with the undercut having a downward taper, the projecting member 14 generates a downward force when the partial dental prosthesis comes off from the alveolus ridge, so that the partial dental prosthesis is stably and steadily supported on the alveolus ridge. The words "retentive tooth" means a tooth which is anchored to the alveolus ridge, such as a natural tooth, a natural tooth crowned with a metal or an artificial tooth.

The elastic lining layer 13 may be adherred to the inner surface of the denture base 3 by using an adhesive which is harmless for human bodies. On the other hand, the elastic lining layer 13 may be formed by poring a molten elastic material to the inner surface of the denture base 3, and then, pressing the elastic material to the inner surface of the denture base 3. In those cases for obtaining a large adhesive strength, it is necessary that the material of the denture base 3 is equal or near in material of the elastic lining layer 13 in value of solubility parameter (hereinafter refferred to as "SP value"). For example, when using polymethylmethacrylate (SP value: 9.3 to 9.9) as the material of the denture base 3, the thermoplastic urethane elastomer (SP value: 10.0) can be employed for the elastic lining layer 13. Examples of the material for the denture base other than polymethylmethacrylate which are compatible with the thermoplastic urethaneelastomer are, for instance, polyethersulfone (SP value: 9.7 to 9.9), polysulfone (SP value: 9.9), polycarbonate (SP value: 9.8), and the like. Such a thermoplastic urethane elastomer is heated to not less than about 100° C. to be softened or molten, coated to the inner surface of the denture base 3, and then, hardened on the denture base 3.

As the adhesive used when the elastic lining layer 13 is adherred to the denture base 3, there may be preferably employed an adhesive which is prepared by using materials which are equal or near to each other in SP value as the material of the denture base 3 and the material of the elastic lining layer 13 and dissolving the above materials into a solvent which can dissolving the above materials. The solvent for the adhesive preferably has an equal or near SP value to those of the materials to be dissolved. Examples of the solvent for the adhesive are, for instance, tetrahydrofuran (SP value: 9.9), n-methyl-pyrrolidone (SP: 9.8), cyclohexane (SP: 9.9), and the like. When using such an adhesive, the adhesion strength can be increased.

The projecting member 14 and the elastic lining layer 13 are integrally formed by means of the following procedure. That is to say, a space for the denture base corresponding to a prepared model of the denture base is formed between a pair of flasks filled with gypsum according to the conventional procedure. The prepared model of the denture base has an end portion corresponding to the shape of the undercut of the retentive tooth so that the space for the denture base includes a space for the projecting member. The space for the projecting member may be a little large in order that the projecting member is elastically in contact with the undercut of the retentive tooth. Subsequently, a thermoplastic elastomer softened by heating is put on a surface of a jaw model side of the flask filled with gypsum, and then, pressed and made thin by using a pallet or the like so that the space for the projecting member is filled with the thermoplastic elastomer and the thickness of the thermoplastic elastomer becomes about 0.5 to 1.5 mm. In that case, the side portion of the artificial tooth may be partially cut and filled with the thermoplastic elastomer in this procedure so that the projecting member has a requried thickness. After the thermoplastic elastomer is cooled, an adhesive is applied to the surface thereof. Thereafter, the space for the denture base is filled with polymethylmethacrylate like a rice cake prepared by blending polymethylmethacrylate powder with liquid methylmethacrylate monomer, and the polymethylmethacrylate like the rice cake is cured under 100°-130° C. of a hot water or a steam, so that the denture base 3 is formed. At the same time, the elastic lining layer 13 and the projecting member 14 are adherred to the denture base 3. Since the artificial tooth 2 is generally made of polymethylmethacrylate, the elastic lining layer 13 and the projecting member 14 made of the thermoplastic elastomer can be also adherred to the artificial tooth 2.

On the other hand, in case of not using an adhesive, the denture base made of polymethylmethacrylate is previously formed in the state that the space for the elastic lining layer 13 and the projecting member 14 are remained, and then, polymethylmethacrylate ressolved in a solvent is applied to an inner surface of the denture base 3, and thereafter, a molten thermoplastic elastomer is pored into the space.

The hardness of the elastic lining layer 13 and the projecting member 14 can be determined in dependence on various case in a range of 50 to 80 in JIS A hardness.

Figure 5:
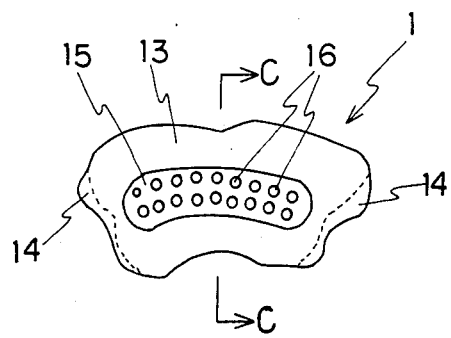
FIG. 5 is a plan view showing another embodiment of the partial dental prosthesis of the present invention.
Figure 6:
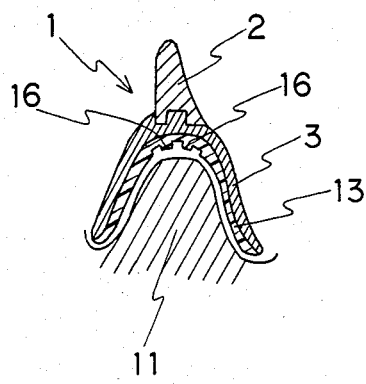
FIG. 6 is a sectional view taken along a line C—C in FIG. 5.
Figure 7:
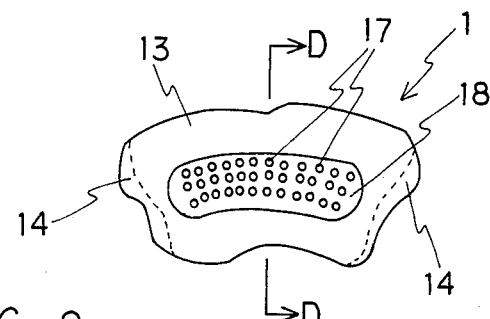
FIG. 7 is a plan view showing an embodiment of the partial dental prosthesis of the present invention.
Figure 8:
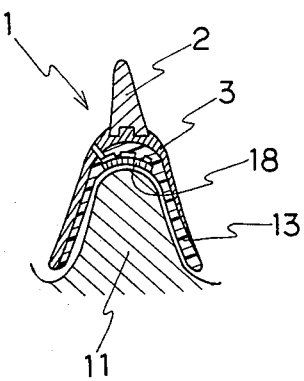
FIG. 8 is a sectional view taken along a line D—D in FIG. 7.

FIGS. 5 and 6 show a modification of the partial dental prosthesis of the present invention. A recess portion 15 is formed on the lower surface of the elastic lining layer 13. A number of small projections 16 are provided on the lower surface of the recess portion 15. When the patial dental prosthesis 1 is put on the alveolus ridge 11, a sealed chamber defined by the recess portion 15 and the alveolus ridge 11 functions as a sucking chamber. Namely, the inner pressure of the sealed chamber is reduced due to mastication movement, so that the sealed chamber of the partial dental prosthesis 1 suckes the corresponding portion of the alveolus ridge 11. In general, the repeated mastication movement causes the alveolous gingiva to come into the recess portion 15 and the recess portion 15 is filled with the alveolus gingiva, which makes the sucking force reduced. However, according to this embodiment, the small projections 16 prevent the alveolus gingiva from coming into the recess portion 15. The small projection is made of an elastic material and the height of it is equal to or lower than the depth of the recess portion. Accordingly, the sealed chamber can maintain its reduced pressure for a long time, and therefore, the sucking function is maintained for a long time. Further, the elastic lining layer 13 is deformably compressed by the pressure applied to the partial dental prosthesis 1 during the mastication movement, so that the volume of the sealed chamber is widely decreased and increased, repeatedly. Since the large variation of the volume makes the sucking force greater, the partial dental prosthesis 1 more strongly suckes the alveolus ridge 11. The recess portion 15 may be divided into several sections to give them individual sucking functions.

FIGS. 7, 8, 9A and 9B show another modification of the partial dental prosthesis of the present invention. The above described recess portion 15 is covered with a plate 18 provided with a number of small apertures 17. The plate 18 may be made of a metal mesh, a porous metal plate, a synthetic resin mesh, a synthetic resin plate, a rubber plate, or the like. The plate 18 has an elasticity that the shape of the plate returns to the original shape after the plate 18 sustains pressure due to mastication movement or sucking force due to the sealed chamber. The plate 18 may be a rigid plate which is not deformed by the mastication movement or the sucking force due to the sealed chamber. The plate 18 may be detachable from the recess portion 15. The elastic lining layer 13 has a number of small projections 16 within the recess portion. According to such a structure, the alveolus gingiva is surely prevented from coming into the sealed chamber, so that the sucking force can be maintained larger.

Figure 9A:
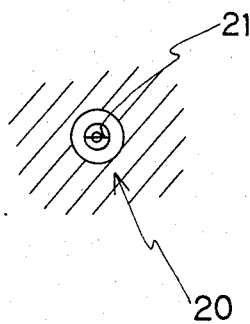
FIG. 9A is a partially enlarged view of a valve means of the partial dental prosthesis shown in FIG. 7.
Figure 9B:
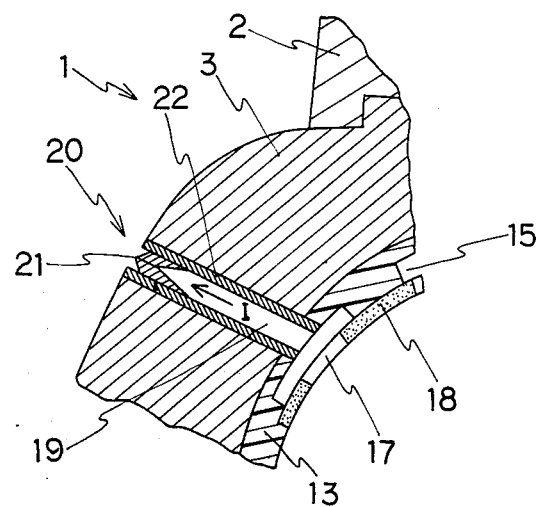
FIG. 9B is a sectional view of the valve means shown in FIG. 9A.

Numeral 19 indicates a small bore communicating the recess portion 15 with an exterior of the denture base 3. The small bore 19 is provided with a check valve 20. The check valve 20 is provided near the exit of the small bore 19, and made of a soft elastic material such as a rubber. As shown in FIGS. 9A and 9B, the check valve 20 has a triangle section, and the top of the triangle apart from the denture base projects to a direction of the exterior surface of the denture base. The check valve 20 is divided into two pieces along a diameter, i.e. a cutting line 21. Narrow bores in the form of point can be employed instead of the cutting line 21. Air and saliva to be exhausted from the recess portion 15 pushes and opens the check valve 20, and is exhausted to the exterior through the cutting line 21. In case of the narrow bores, air or saliva pushes and opens the narrow bores and is exhausted to the exterior through the narrow bores. This check valve 20 allows air or saliva to pass from the recess portion 15 to the exterior of the denture base 3, i.e. in the direction of the arrow I in FIG. 9B, but the check valve 20 prevents their counter flow, i.e. the flow from the exterior of the denture base 3 to the recess portion 15. An outer surface of the check valve 20 is preferably shaped so as to have a gradually curved surface in order to clean in ease and to prevent dregs in the mouth from sticking on the outer surface. Numeral 22 indicates a cylindrical body made of a synthetic resin, for example, the same material as the denture base. The cylindrical body 22 with the check valve 22 is inserted into the small bore 19.

In operation of such a structure, the elastic lining layer 13 is deformably compressed by the pressure applied to the partial dental prosthesis 1 due to mastication movement. At the same time, the sealed chamber is also compressed. As a result, air in the sealed chamber is partially exhausted to an exterior through the small bore 19 and the check valve 20. Then, when the pressure applied to the partial dental prosthesis 1 is removed, the shape of the elastic lining layer 13 is returned to the original shape and the volume of the sealed chamber is increased, which makes the pressure in the sealed chamber reduced. Consequently, the partial dental prosthesis 1 is stably and steadily supported on the alveolus ridge 11 by the strong sucking force. In such a way, since the operation of exhausting air or saliva through the small bore 19 is effected at every mastication movement, the sucking force is maintained or increased, and thus, the strong sucking force can be obtained.

Figure 10:
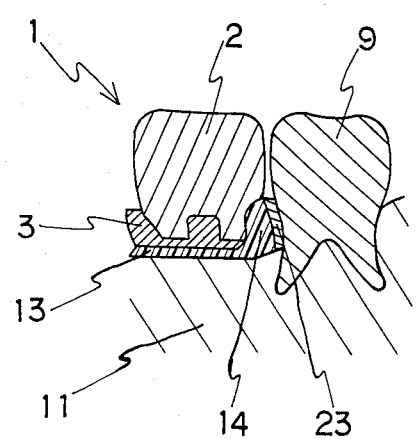
FIG. 10 is a partial sectional view showing an embodiment of the partial dental prosthesis of the present invention.
Figure 11:
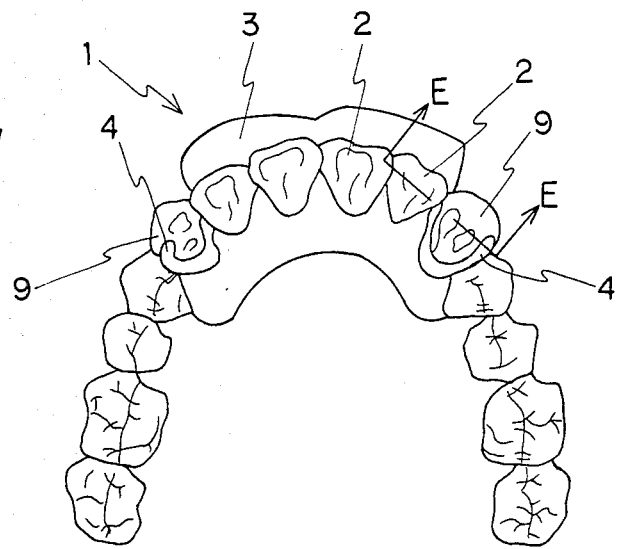
FIG. 11 is a plan view showing a conventional partial dental prosthesis.
Figure 12:
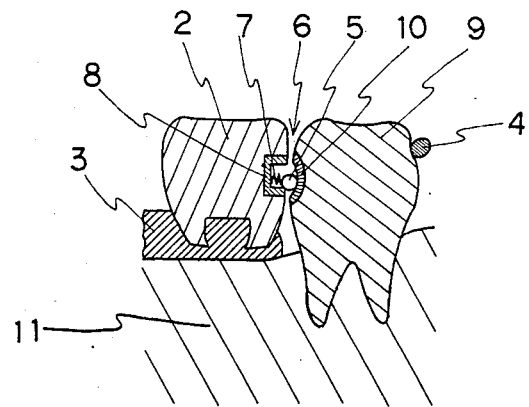
FIG. 12 is a sectional view taken along a line E—E in FIG. 11.

FIG. 10 shows another embodiment of the partial dental prosthesis of the present invention. A covering layer 23 having a low friction is provided on the surface of the projecting member 14, i.e. the surface of the projecting member contacting to the undercut of the natural tooth 9. As the material of the covering layer 23, there can be preferably employed a dental metal such as alloy of Ni-Co containing Au or a rigid resin such as polymethylmethacrylate or polyethersulphone. According to the structure, the removing and setting operation of the partial dental prosthesis within the mouth can be smoothly achieved.

According to the present invention, the following effects can be obtained.

(1) A load applied to the retentive tooth adjacent to the partial dental prosthesis is much reduced, since the partial dental prosthesis is fixed by the engagement between the projecting member and the undercut of the adjacent retentive tooth so that the denture retention can be uniformly caused to the undercut of the adjacent retentive tooth. In the conventional clasp, the clasp tends to be deformed by movement of the partial dental prosthesis in the mouth and by the force applied when removing and setting the partial dental prosthesis, since the clasp is anchored to a bilge or a belly of the adjacent retentive tooth. However, according to the partial dental prosthesis of the present invention, uniform fixing force can be obtained. Further, when using the clasp alone, the force applied to the adjacent retentive tooth is not uniform and concentrated on the specific area of the retentive tooth, so that the life span of the adjacent retentive tooth is shortened. However, according to the present invetion, not only the fixing force due to the clasp can be made to be reduced, but also the projecting member causes the uniform denture retention to the contact surface of the adjacent retentive tooth. Also, since this denture retention is caused to the undercut by being closely or elastically in contact with the undercut, the pressure applied to the adjacent retentive tooth can be reduced.

(2) The projecting member and the sucking means of the present invention can be substantially substituted for the clasp, so that the clasp can be reduced in size and weight. Therefore, the modification of the adjacent natural tooth such as cutting can be minimized.

(3) The partial dental prosthesis is stably and steadily supported on the alveolus ridge by the projecting member and the sucking means. Even if the clasp is deformed by setting and removing the partial dental prosthesis, the desired stable and steady state of the partial dental prosthesis can be maintained.

(4) The projecting member also generates a downward force when the partial dental prosthesis comes off from the alveolus ridge, so that the partial dental prosthesis is stably and steadily supported on the alveolus ridge, since the projecting member is closely or elastically in contact with the undercut having a downward taper.

(5) The aesthetic purpose can be improved, since only a small clasp provided at least at tongue side of the patient can serve its function.

(6) The patient does not unpleasantly feel the clasp as an extraneous substance, since the size of the clasp is reduced.

(7) Even if the partial dental prosthesis is shaken during mastication movement, the uncomfortable tenderness can be reduced, since the projecting member of the partial dental prosthesis is closely or elastically in contact with the adjacent retentive tooth.

(8) It is easy to maintain the cleanness of the partial dental prosthesis. Further, the endurance of the partial dental prosthesis can be increased, and at the same time, the cost can be reduced, since it is not necessary to employ the conventional attachment.

(9) The unpleasantness which is felt when seting the partial dental prosthesis in the mouth can be reduced, since the size of the denture base is made small.

What is claimed is:

1. In a partial dental prosthesis comprising artificial teeth and a denture base holding said artificial teeth, wherein at least one end of the partial dental prosthesis is adjacent to a retentive tooth, the improvement which comprises a projecting member made of an elastomeric material provided at said denture base and at least one end of said partial dental prosthesis between said prosthesis and adjacent retentive tooth, said projecting member having an inclined end surface in contact with a tapered portion of said retentive tooth so as to be tapered toward said retentive tooth, whereby the partial dental prosthesis is urged toward said alveolus ridge and stably and steadily supported on an alveolus ridge of a patient.

2. The partial dental prosthesis of claim 1, wherein said projecting member has a covering layer having a low friction on its surface.

3. In a partial dental prosthesis comprising artificial teeth and a denture base holding said artificial teeth, wherein at least one end of the partial dental prosthesis is adjacent to a retentive tooth, the improvement which comprises a projecting member made of an elastomeric material provided at said at least one end of said partial dental prosthesis between said prosthesis and the adjacent retentive tooth, said projecting member having an inclined enlarged end surface in contact with a tapered portion of said retentive tooth portion said retentive tooth, and an elastomeric layer made of an elastomeric material on an inner surface of said denture base and integrally formed with said projecting member, whereby the partial dental prosthesis is urged toward said alveolus ridge and stably and steadily supported on said alveolus ridge of a patient and fitted to the alveolus ridge by means of said elastic lining layer.

4. The partial dental prosthesis of claim 3, wherein said elastomeric lining layer has a recess portion defining a sealed chamber with the alveolus ridge and has means for preventing an alveolus gingiva from coming into said recess portion.

5. The partial dental prosthesis of claim 4, further comprising a small bore communicating said recess portion with an exterior through said elastomeric lining layer and said denture base, and a valve means for passing air or saliva from said recess portion to the exterior of the denture base.

6. The partial dental prosthesis of claim 4, wherein said means for preventing an alveolus gingiva from coming into said recess portion is a number of small projections made of an elastomeric material which are provided within said recess portion, and the height of each of said small projections is equal to or lower than the depth of said recess portion.

7. The partial dental prosthesis of claim 4, wherein said means for preventing an alveolus gingiva from coming into said recess portion is a plate covering said recess portion and having a number of small apertures, and the outline of said plate corresponds to the outline of the alveolus ridge.

* * * * *